United States Patent
Bentley et al.

(10) Patent No.: US 11,103,438 B2
(45) Date of Patent: Aug. 31, 2021

(54) HAIR COMPOSITION

(71) Applicant: Conopco, Inc., Englewood Cliffs, NJ (US)

(72) Inventors: Christopher David Bentley, Liverpool (GB); Lalitesh Chandra, Bedford (GB); Llyr Glyndwr Griffiths, Rhos-on-Sea (GB); Janet Drobits Windisch, Collegeville, PA (US); Lynsey Joanne Coan, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 996 days.

(21) Appl. No.: 15/543,684

(22) PCT Filed: Jan. 13, 2016

(86) PCT No.: PCT/EP2016/050582
§ 371 (c)(1),
(2) Date: Jul. 14, 2017

(87) PCT Pub. No.: WO2016/113316
PCT Pub. Date: Jul. 21, 2016

(65) Prior Publication Data
US 2017/0367962 A1     Dec. 28, 2017

(30) Foreign Application Priority Data
Jan. 16, 2015 (EP) .................................. 15151489

(51) Int. Cl.
| | |
|---|---|
| *A61Q 5/02* | (2006.01) |
| *A61Q 5/06* | (2006.01) |
| *A61Q 5/12* | (2006.01) |
| *A61K 8/81* | (2006.01) |
| *A61K 8/06* | (2006.01) |
| *A61K 8/02* | (2006.01) |

(52) U.S. Cl.
CPC .......... *A61K 8/8147* (2013.01); *A61K 8/0241* (2013.01); *A61K 8/0291* (2013.01); *A61K 8/06* (2013.01); *A61K 8/8152* (2013.01); *A61Q 5/02* (2013.01); *A61Q 5/06* (2013.01); *A61Q 5/12* (2013.01); *A61K 2800/34* (2013.01); *A61K 2800/412* (2013.01); *A61K 2800/413* (2013.01); *A61K 2800/54* (2013.01)

(58) Field of Classification Search
None
See application file for complete search history.

(56) References Cited

U.S. PATENT DOCUMENTS

| | | | |
|---|---|---|---|
| 2003/0108501 A1* | 6/2003 | Hofrichter | A61K 8/044 424/70.1 |
| 2004/0057823 A1 | 3/2004 | Rollat et al. | |
| 2007/0140991 A1* | 6/2007 | Maitra | A61K 8/8152 424/53 |
| 2013/0344006 A1* | 12/2013 | Akinpelu | A61Q 5/12 424/47 |

FOREIGN PATENT DOCUMENTS

| | | |
|---|---|---|
| CN | 1561379 A | 1/2005 |
| CN | 103476393 A | 12/2013 |
| EP | 1321130 | 6/2003 |
| FR | 2991581 | 12/2013 |
| JP | 2009520708 A | 5/2009 |
| JP | 2014505083 A | 2/2014 |
| JP | 2014505084 A | 2/2014 |
| JP | 2014505085 A | 2/2014 |
| WO | WO03026599 | 4/2003 |
| WO | WO03028677 | 4/2003 |
| WO | WO2007071308 | 6/2007 |
| WO | 2012107366 A | 8/2012 |
| WO | 2012107367 A | 8/2012 |
| WO | WO2012107368 | 8/2012 |
| WO | WO2013186720 | 12/2013 |
| WO | 2014/143728 A1 | 9/2014 |
| WO | 2014/143757 A1 | 9/2014 |

OTHER PUBLICATIONS

Search Report & Written Opinion in PCTEP2016050582, dated Mar. 29, 2016.
Search Report in EP15151489, dated May 13, 2015.
Written Opinion in EP15151489, dated May 13, 2015.

* cited by examiner

*Primary Examiner* — Jyothsna A Venkat
(74) *Attorney, Agent, or Firm* — Wiggin and Dana LLP; Anthony D. Sabatelli; Brian A. Pattengale

(57) ABSTRACT

A rinse off hair treatment composition comprising;
 a. a pressure sensitive adhesive emulsion comprising one or more pressure sensitive polymer, wherein the pressure sensitive polymer is not silicone pressure sensitive polymer, and
 b. at least one material selected from the group consisting of
  i) a hair conditioning agent;
  ii) a hair cleansing agent, and,
 c. a deposition aid.

10 Claims, No Drawings

HAIR COMPOSITION

STATEMENT OF INVENTION

The present invention relates to a rinse-off hair treatment composition comprising pressure sensitive adhesive components.

BACKGROUND

Consumers desire styling and restyling benefits from hair products. These are traditionally delivered by post-wash, leave-on treatments such as gels, sprays, waxes, mousses and creams. Such products require an extra step in a consumer's hair care routine, which can be time consuming.

Rinse off formulations comprising styling benefit agents have previously been incorporated into rinse-off hair treatments however the results have been unsatisfactory. Products either have minimal effect or cause the hair to be harsh, dull and dry feeling.

WO 03/028677 discloses an aqueous hair treatment composition comprising: a) at least one silicone pressure sensitive adhesive; and b) at least one material selected from the group consisting of a hair conditioning agent, a hair conditioning agent, a hair cleansing agent, and an agent for hair care suspension, is described.

WO 03/026599 discloses personal care compositions for rinse-off application to the hair, nails or skin. These compositions comprise a silicone-resin based adhesive including a silicone resin copolymer as a condensation product of an organosiloxane fluid and a silicone resin; a cleansing surfactant; and a carrier liquid. The personal cleansing compositions can also comprise as the silicone-resin based adhesive, in addition to or in place of the silicone resin copolymer, a combination of an organosiloxane resin and a diorganosiloxane fluid at a weight ratio of said fluid of from 1:9 to about 10:1. The personal cleansing compositions provide hair styling benefits when applied to the hair, and when applied to the skin, barrier protection from surfactants or other materials having skin irritation potential.

It has now been found that non-silicone pressure sensitive adhesive emulsions can be incorporated into a rinse off hair treatment to impart superior styling and restyling benefits. In particular improved frictionalising and style creation. The hair is left feeling soft and when the original style is lost the hair can be restyled with simple intervention, without using any additional water, product or heat.

SUMMARY OF THE INVENTION

A rinse off hair treatment composition comprising;
a) a pressure sensitive adhesive emulsion comprising one or more pressure sensitive polymer, wherein the pressure sensitive polymer is not silicone pressure sensitive polymer, and
b) at least one material selected from the group consisting of
   i) a hair conditioning agent; and
   ii) a hair cleansing agent, and
c) a deposition aid.

DETAILED DESCRIPTION

Pressure Sensitive Adhesives

"Pressure sensitive adhesives" (PSA) materials are permanently tacky at room temperatures and able to develop measurable adhesion to a surface simply upon contact or by the application of a light pressure. Generally they do not require heat. No chemical reaction takes place between the adhesive and the adherent, no curing of the adhesive is necessary and no solvent is required to be lost during the adhesion process.

The pressure sensitive adhesive for use in the present invention are not intended to include "silicone pressure sensitive adhesives" which are a combination of a polymer or gum and a tackifying resin. The polymer or gum being an organosiloxane and/or a block copolymer comprising an organosiloxane.

The pressure sensitive adhesive for use in the composition of the current invention is in the form of an emulsion, more preferably an aqueous emulsion. The emulsion may be anionic, cationic, non-ionic, zwitterionic or amphoteric. The emulsion is preferably anionic.

The pressure sensitive adhesive emulsion comprises particles of pressure sensitive adhesive material. The particle size of the pressure sensitive adhesive particles is preferably 1 nm to 1 um, more preferably 10 nm to 750 nm, even more preferably 100 nm to 500 nm and most preferably 200 nm to 400 nm.

The rinse off hair treatment composition preferably comprises 0.01 to 10 w.t. % active pressure sensitive adhesive (i.e. not including the weight of the emulsion liquid), more preferably 0.1 to 7 w.t. %, most preferably 0.25 to 5 w.t. %.

The pressure sensitive adhesive in the emulsion may be one type of pressure sensitive polymer or a combination of different pressure sensitive polymers. The pressure sensitive polymers may be hydrophilic or hydrophobic.

Preferred hydrophobic pressure sensitive polymers are; Poly(isobutylene) pressure sensitive adhesives, acrylic pressure sensitive adhesives, rubber block copolymer pressure sensitive adhesives and ethylene-vinyl acetate pressure sensitive adhesives.

Preferred hydrophilic pressure sensitive polymers are; Poly(vinyl pyrrolidone) pressure sensitive adhesives (PVP Hydrogels), Poly(vinyl alcohol) pressure sensitive adhesives (PVA hydrogels), Polymethyl methacrylate pressure sensitive adhesives (PMMA hydrogels).

Poly(isobutylene) PSAs or PIB are homopolymers of isobutylene. Suitable poly(isobutylene) PSAs are available commercially for example by ExxonMobile Chemical under the trade name Vistanex™.

Rubber block copolymer PSAs generally comprise 3 blocks; A-B-A. Wherein A is an amorphous polymer with a Tg above room temperature and B is an amorphous polymer with Tg lower than room temperature. Examples of rubber block copolymer PSAs include poly(styrene-isoprene-styrene), SIS, and poly(styrene-butadiene-styrene), SBS.

Ethylene-vinyl acetate PSAs are a copolymer of ethylene and vinyl acetate. Pressure sensitive ethylene-vinyl acetates have a relatively high content of vinyl acetate.

Poly(vinyl pyrrolidone) PSAs or PVP hydrogels are obtained by blending high molecular weight poly(vinyl pyrrolidone), PVP, with low molecular weight poly(ethyleneglycol), PEG. Poly(vinyl alcohol) PSAs or PVA hydrogels can be produced by freeze-thaw techniques using $Ca^{2+}$ ions.

Polymethyl methacrylate PSAs or PMMA hydrogels can be formed from an interaction between poly(vinyl pyrrolidone) and polymethyl methacrylate.

The pressure sensitive adhesives of the current invention are preferably an acrylic PSA.

Acrylic pressure sensitive adhesives are random copolymers comprising;

i) An acrylic group having a side chain of 4 or more carbons
ii) A side chain acrylic, preferably a $C_1$-$C_6$ side-chain acrylic Examples of an acrylic group having a side chain of at least 4 carbons include n-butyl acrylate and 2-ethylhexyl acrylate, n-hexyl acrylate, Isooctyl acrylate and Dodecyl acrylate. Preferred acrylic group having a side chain of 4 or more carbons are butyl acrylate and 2-ethyl hexyl acrylate. Most preferred is butylacrylate.

Examples of a $C_1$-$C_6$ side-chain acrylic include acrylic acid, methyl acrylate, methyl methacrylate, ethyl acrylate, butyl acrylate. Preferred a $C_1$-$C_6$ side-chain acrylic are Ethyl acrylate, butylacrylate and methacrylic acid. Most preferred is methacrylic acid.

Suitable water borne acrylic pressure sensitive adhesives include Dow Corning PA-0560, Dow Corning PA-0580, Dow Corning MG-0560, Dow Corning MG-0580, NACOR 38-088A ex National Starch and Chemical, Acudyne MD-5800 by Dow, Acudyne MD-5600 by Dow, Tackwhite NA 55 ex Ichemco srl, Tackwhite A 4 MED ex Ichemco srl, Acronal 80 D ex BASF AG, Acronal 85 D BASF AG, Acronal A220 exBASF AG, Acronal N 285 ex BASF AG, Acronal V 210 ex BASF AG and Acronal V212 ex BASF AG.

Particularly preferred acrylic pressure sensitive materials include Acudyne MD-5800 by Dow and Acudyne MD-5600 by Dow.

The pressure sensitive adhesive of the current invention preferably has a dynamic storage (G') value of $10^3$ Pa to $10^6$ Pa.

The pressure sensitive adhesive of the current invention preferably has a dissipation (G") value of $10^3$ Pa to $10^6$ Pa.

The glass transition temperature of the pressure sensitive adhesive is preferably $-100°$ C. to $20°$ C., more preferably $-80°$ C. to $0°$ C. and most preferably $-60°$ C. to $-30°$ C.

Hair Cleansing Agent

Compositions according to the current invention may comprise one or more hair cleansing agents.

Anionic Cleansing Surfactant:

The hair cleansing agent may be an anionic cleansing surfactant which is cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alphaolefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic cleansing surfactants for use in compositions of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, sodium lauryl ether sulphate(n)EO, (where n ranges from 1 to 3), ammonium lauryl sulphate and ammonium lauryl ether sulphate (n)EO, (where n ranges from 1 to 3).

Mixtures of any of the foregoing anionic cleansing surfactants may also be suitable.

The total amount of anionic cleansing surfactant in compositions of the invention is generally from 1 to 30 w.t. %, preferably from 6 to 20 w.t. %, more preferably from 8 to 16 w.t. %.

Amphoteric Surfactants:

The composition can include other cleansing agents, to help impart aesthetic, physical or cleansing properties to the composition. A preferred example is an amphoteric or zwitterionic surfactant, which can be included in an amount ranging from 0 to 8 w.t. %, preferably from 1 to 4 w.t. %. Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

Nonionic Surfactants:

Another preferred example is a nonionic surfactant, which can be included in an amount ranging from 0 to 8 w.t. %, preferably from 2 to 5 w.t. %.

For example, representative nonionic surfactants that can be included in compositions of the invention include condensation products of aliphatic ($C_8$-$C_{18}$) primary or secondary, linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolarnide and coco mono-isopropanolamide.

Further nonionic surfactants which can be included in compositions of the invention are the alkyl polyglycosides (APGs). Typically, the APG is one which comprises an alkyl group connected (optionally via a bridging group) to a block of one or more glycosyl groups. Preferred APGs are defined by the following formula:

RO-(G)$n$ wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerization, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in compositions of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy 20 fatty acid amides, such as $C_{10}$-$C_{18}$ N-(3-methoxypropyl) glucamide.

Hair Conditioning Agent

Compositions according to the current invention may comprise conditioning agents. Conditioning agents are selected from cationic surfactants, used singly or in admixture.

Cationic surfactants useful in compositions of the invention contain amino or quaternary ammonium hydrophilic moieties which are positively charged when dissolved in the aqueous composition of the present invention.

Examples of suitable cationic surfactants are those corresponding to the formula:

$$[N(R_1)(R_2)(R_3)(R_4)]^+(X)^-$$

in which $R_1$, $R_2$, $R_3$ and $R_4$ are independently selected from (a) an aliphatic group of from 1 to 22 carbon atoms, or (b) an aromatic, alkoxy, polyoxyalkylene, alkylamido, hydroxyalkyl, aryl or alklaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for compositions of the present invention are monoalkyl quarternary ammonium compounds in which the alkyl chain lengthy is $C_8$ to $C_{14}$.

Suitable examples of such materials correspond to the formula:

$$[N(R_5)(R_6)(R_7)(R_8)]^+(X)^-$$

in which $R_5$ is a hydrocarbon chain having 8 to 14 carbon atoms or a functionalised hydrocarbyl chain with 8 to 14 carbon atoms and containing ether, ester, amido or amino moieties present as substituents or as linkages in the radical chain, and $R_6$, $R_7$ and $R_8$ are independently selected from (a) hydrocarbyl chains of from 1 to about 4 carbon atoms, or (b) functionalised hydrocarbyl chains having from 1 to about 4 carbon atoms and containing one or more aromatic, ether, ester, amido or amino moieties present as substituents or as linkages in the radical chain, and X is a salt-forming anion such as those selected from halogen, (e.g. chloride, bromide), acetate, citrate, lactate, glycolate, phosphate nitrate, sulphate and alkylsulphate radicals.

The functionalised hydrocarbyl chains (b) may suitably contain one or more hydrophilic moieties selected from alkoxy (preferably $C_1$-$C_3$ alkoxy), polyoxyalkylene, alkylester, and combinations thereof.

Preferably the hydrocarbon chains $R_1$ have 12 to 14 carbon atoms, most preferably 12 carbon atoms. They may be derived from source oils which contain substantial amounts of fatty acids having the desired hydrocarbyl chain length. For example, the fatty acids from palm kernel oil or coconut oil can be used as a source of $C_8$ to $C_{12}$ hydrocarbyl chains.

Typical monoalkyl quarternary ammonium compounds of the above general formula for use in compositions of the invention include:

i) Lauryl trimethylammonium chloride (available commercially as Arquad C35 ex Akzo); cocodimethyl benzyl ammonium chloride (available commercially as Arquad DMCB-80 ex-Akzo)

ii) Compounds of the formula:

$$[N(R_1)(R_2)((CH_2CH_2O)_xH)((CH_2CH_2O)_yH]^+(X)^-$$

wherein:

x+y is an integer from 2 to 20;

$R_1$ is a hydrocarbyl chain having 8 to 14, preferably 12 to 14, most preferably 12 carbon atoms and containing ether, ester, amido or amino moieties present as substituent's or as linkages in the radical chain;

$R_2$ is a $C_1$-$C_3$ alkyl group or benzyl group, preferably methyl, and X is a salt-forming anion such as those selected from halogen, (e.g. chloride, bromide), acetate, citrate, lactate, glycolate, phosphate nitrate, sulphate, methosulphate and alkylsulphate radicals.

Suitable examples are PEG-n lauryl ammonium chlorides (where n is the PEG chain length), such as PEG-2 cocomonium chloride (available commercially as Ethoquad C12 ex-Akzo Nobel); PEG-2 cocobenzyl ammonium chloride (available commercially as Ethoquad CB12 ex-Akzo Nobel); PEG-5 cocomonium methosulphate (available commercially as Rewoquat CPEM ex Rewo); PEG-15 cocomonium chloride (available commercially as Ethoquad C/25 ex-Akzo).

i) Compounds of the formula:

$$[N(R_1)(R_2)(R_3)((CH_2)_nOH)]^+(X)^-$$

wherein:

n is an integer from 1 to 4, preferably 2;

$R_1$ is a hydrocarbyl chain having 8 to 14, preferably 12 to 14, most preferably 12 carbon atoms;

$R_2$ and $R_3$ are independently selected from $C_1$-$C_3$ alkyl groups, and are preferably methyl, and X– is a salt-forming anion such as those selected from halogen, (e.g. chloride, bromide), acetate, citrate, lactate, glycolate, phosphate nitrate, sulphate, alkylsulphate radicals.

Suitable examples are lauryldimethylhydroxyethylammonium chloride (available commercially as Prapagen HY ex-Clariant).

Mixtures of any of the foregoing cationic surfactants compounds may also be suitable.

Examples of suitable cationic surfactants for use in hair compositions of the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in hair compositions of the invention is cetyltrimethylammonium chloride, available commercially, for example as DEHYQUART, ex Henkel.

In the compositions of the invention, the level of cationic surfactant is preferably from 0.01 to 10, more preferably 0.05 to 5, most preferably 0.1 to 2 w.t. % of the total composition.

Deposition Polymer

The composition of the present invention may be a shampoo, shampoo compositions of the current invention comprise a deposition polymer.

The deposition polymer may be a homopolymer or be formed from two or more types of monomers. The molecular weight of the polymer will generally be between 5 000 and 10,000,000, typically at least 10 000 and preferably in the range 100 000 to about 2,000,000. The deposition polymers will be cationic polymers. The deposition polymers will have cationic nitrogen containing groups such as quaternary ammonium or protonated amino groups, or a mixture thereof.

The cationic nitrogen-containing group will generally be present as a substituent on a fraction of the total monomer units of the deposition polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable deposition polymers include, for example, copolymers of vinyl monomers having cationic amine or quaternary ammonium functionalities with water soluble spacer monomers such as (meth) acrylamide, alkyl and dialkyl (meth) acrylamides, alkyl (meth) acrylate, vinyl caprolactone and vinyl pyrrolidine. The alkyl and dialkyl substituted monomers preferably have $C_1$-$C_7$ alkyl groups, more preferably $C_{1-3}$ alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The deposition polymers can comprise mixtures of monomer units derived from amine- and/or quaternary ammonium-substituted monomer and/or compatible spacer monomers.

Suitable deposition polymers include, for example:
copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);
copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);
cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;
mineral acid salts of amino-alkyl esters of homo- and copolymers of unsaturated carboxylic acids having from 3 to 5 carbon atoms, (as described in U.S. Pat. No. 4,009,256);
cationic polyacrylamides (as described in WO95/22311).

Other deposition polymers that can be used include cationic polysaccharide polymers, such as cationic cellulose derivatives, cationic starch derivatives, and cationic guar gum derivatives. Suitably, such cationic polysaccharide polymers have a charge density in the range from 0.1 to 4 meq/g. Cationic polysaccharide polymers suitable for use in compositions of the invention include those of the formula:

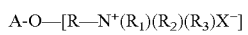

$$A-O-[R-N^+(R_1)(R_2)(R_3)X^-]$$

wherein: A is an anhydroglucose residual group, such as a starch or cellulose anhydroglucose residual. R is an alkylene, oxyalkylene, polyoxyalkylene, or hydroxyalkylene group, or combination thereof. $R_1$, $R_2$, and $R_3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R_1$, $R_2$ and $R_3$) is preferably about 20 or less, and X− is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the deposition polymer is selected from cationic cellulose and cationic guar gum derivatives. More preferably the deposition polymer is a cationic guar gum derivative. Particularly preferred deposition polymers are JAGUAR C13S, JAGUAR C14S, JAGUAR C15, JAGUAR C17 and JAGUAR C16 and JAGUAR C162. The composition of the invention may be a conditioner. Deposition aids for use in conditioners of the invention are preferably selected from cationic surfactants, used singly or in admixture.

Cationic surfactants useful in compositions for use in the method of the invention contain amino or quaternary ammonium hydrophilic moieties which are positively charged when dissolved in aqueous composition.

Examples of suitable cationic surfactants are those corresponding to the formula

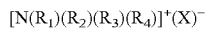

$$[N(R_1)(R_2)(R_3)(R_4)]^+(X)^-$$

in which $R_1$, $R_2$, $R_3$ and $R_4$ are independently selected from (a) an aliphatic group of from 1 to 22 carbon atoms, or (b) an aromatic, alkoxy, polyoxyalkylene, alkylamido, hydroxyalkyl, aryl or alklaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for compositions for use in the method of the present invention are monoalkyl quarternary ammonium compounds in which the alkyl chain lengthy is $C_8$ to $C_{14}$.

Suitable examples of such materials correspond to the formula:

$$[N(R_5)(R_6)(R_7)(R_8)]^+(X)^-$$

in which $R_5$ is a hydrocarbon chain having 8 to 14 carbon atoms or a functionalised hydrocarbyl chain with 8 to 14 carbon atoms and containing ether, ester, amido or amino moieties present as substituents or as linkages in the radical chain, and $R_6$, $R_7$ and $R_8$ are independently selected from (a) hydrocarbyl chains of from 1 to about 4 carbon atoms, or (b) functionalised hydrocarbyl chains having from 1 to about 4 carbon atoms and containing one or more aromatic, ether, ester, amido or amino moieties present as substituents or as linkages in the radical chain, and X is a salt-forming anion such as those selected from halogen, (e.g. chloride, bromide), acetate, citrate, lactate, glycolate, phosphate nitrate, sulphate and alkylsulphate radicals.

The functionalised hydrocarbyl chains (b) may suitably contain one or more hydrophilic moieties selected from alkoxy (preferably $C_1$-$C_3$ alkoxy), polyoxyalkylene, alkylester, and combinations thereof.

Preferably the hydrocarbon chains $R_1$ have 12 to 14 carbon atoms, most preferably 12 carbon atoms. They may be derived from source oils which contain substantial amounts of fatty acids having the desired hydrocarbyl chain length. For example, the fatty acids from palm kernel oil or coconut oil can be used as a source of $C_8$ to $C_{12}$ hydrocarbyl chains.

Typical monoalkyl quarternary ammonium compounds of the above general formula for use in compositions for use in the method of the invention include:
(i) Lauryl trimethylammonium chloride (available commercially as Arquad C35 ex Akzo); cocodimethyl benzyl ammonium chloride (available commercially as Arquad DMCB-80 ex-Akzo).
(ii) Compounds of the formula:

$$[N(R_1)(R_2)((CH_2CH_2O)_xH)((CH_2CH_2O)_yH]^+(X)^-$$

wherein:
x+y is an integer from 2 to 20;
$R_1$ is a hydrocarbyl chain having 8 to 14, preferably 12 to 14, most preferably 12 carbon atoms and containing ether, ester, amido or amino moieties present as substituent's or as linkages in the radical chain;
$R_2$ is a $C_1$-$C_3$ alkyl group or benzyl group, preferably methyl, and
X is a salt-forming anion such as those selected from halogen, (e.g. chloride, bromide), acetate, citrate, lactate, glycolate, phosphate nitrate, sulphate, methosulphate and alkylsulphate radicals.

Suitable examples are PEG-n lauryl ammonium chlorides (where n is the PEG chain length), such as PEG-2 cocomonium chloride (available commercially as Ethoquad C12 ex-Akzo Nobel); PEG-2 cocobenzyl ammonium chloride (available commercially as Ethoquad CB12 ex-Akzo Nobel); PEG-5 cocomonium methosulphate (available commercially as Rewoquat CPEM ex Rewo); PEG-15 cocomonium chloride (available commercially as Ethoquad C/25 ex-Akzo).
(iii) Compounds of the formula:

$$[N(R_1)(R_2)(R_3)((CH_2)_nOH)]^+(X)^- \qquad (iv)$$

wherein:
n is an integer from 1 to 4, preferably 2;
$R_1$ is a hydrocarbyl chain having 8 to 14, preferably 12 to 14, most preferably 12 carbon atoms;
$R_2$ and $R_3$ are independently selected from $C_1$-$C_3$ alkyl groups, and are preferably methyl, and
X– is a salt-forming anion such as those selected from halogen, (e.g. chloride, bromide), acetate, citrate, lactate, glycolate, phosphate nitrate, sulphate, alkylsulphate radicals.

Suitable examples are lauryldimethylhydroxyethylammonium chloride (available commercially as Prapagen HY ex-Clariant) Mixtures of any of the foregoing cationic surfactants compounds may also be suitable.

Examples of suitable cationic surfactants for use in hair compositions for use in the method of the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant is cetyltrimethylammonium chloride, available commercially, for example as DEHYQUART, ex Henkel.

Suspending Agents

Compositions in accordance with this invention may optionally be formulated as suspensions for the treatment of hair and subsequent rinsing. These compositions will require a suspending agent.

In an optional embodiment of the current invention, the hair treatment composition further comprises from 0.01 to 10 w.t. % of a suspending agent for the pressure sensitive adhesive. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol (trade mark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Product Form

The composition of the present invention is a rinse-off composition. The term "rinse-off" is used to mean that the composition of the present invention is used in a context wherein the composition is ultimately rinsed or washed from the treated hair. Rinsing may be either after or during the application of the product. The composition is preferably a shampoo or a conditioner composition. Most preferably a shampoo composition.

The present invention relates to rinse-off compositions comprising a pressure sensitive adhesive. Rinse-off compositions are aqueous compositions that are intended for the treatment of the hair that subsequent to their application are rinsed-off with water while leaving a deposit of one or more ingredients on the hair and/or the skin in an amount that provides desirable effects. Typical rinse-off compositions include hair shampoos and hair conditioners. Key features of rinse-off compositions include cleaning effects and lathering effects, and the provision of conditioning effects. Further features of importance include viscosity, homogeneity and stability of the rinse-off composition.

So, the compositions of rinse-off cosmetics are largely determined by the intended application. Accordingly, a rinse-off composition contains various ingredients in order to provide desired physico-chemical properties to the rinse-off composition and to provide desired cosmetic properties and effects for the intended application.

A first class of ingredients for use in the rinse off compositions of the invention is constituted by cleaning (cleansing) agents, including soaps and detergents. The latter include anionic, non-ionic and amphoteric surfactants and mixtures thereof. The cleaning agents having pronounced tensio-active and lather-forming properties, provide a rich foam and promote efficient removal from the hair of contaminants, such as dust, natural fats and residues of transpiration.

A second class of ingredients is constituted by conditioning agents, which are essential ingredients of rinse-off compositions for the treatment of the hair. Conditioning agents minimise static electricity in the hair and make that the hair is easily manageable, easily disentangling, and that the combability of the wet and the dry hair is easy and smooth.

They furthermore, provide body, lustre and softness to the hair. These and other common cosmetic effects are conventionally referred to, also herein, as conditioning properties or conditioning effects. Conditioning agents are cationic-type, anionic-type or non-ionic-type compounds, referred to herein as cationic-, anionic-, and non-ionic conditioning agents, that leave, when the cosmetic composition is rinsed off, a deposit on the hair that provides to the hair desired conditioning properties. Cationic conditioning agents are typically cationic polymers, namely polymeric compounds that contain cationic groups and/or groups that are ionisable in aqueous medium to form cationic groups. Cationic groups are, for example, groups that bear a quaternary nitrogen atom. Accordingly, polymers bearing the latter cationic groups are often named polyquaternium compounds.

By the term cationic polymers is meant herein cationic polymeric conditioning agents. Hair is negatively charged and due to their opposite electrical charge vis-a-vis the hair, cationic polymers easily interact with the hair and leave a deposit on it when cosmetic compositions containing said cationic polymers are rinsed off. The deposit of the cationic polymer on the hair provides the conditioning properties. Besides, cationic polymers are readily soluble in water-based shampoo compositions, which facilitates the preparation of the rinse-off compositions. Anionic conditioning agents typically consist of so-called anionic polymers, namely polymeric compounds that contain units bearing one or more carboxylate groups. Typical anionic conditioning agents are for example alginate salts.

Non-ionic conditioning agents consist of non-ionic-type compounds, including high molecular weight compounds and certain polymeric compounds. Typical non-ionic-type conditioning agents comprise various waxy and oily materials, silicones and silicone-containing copolymers. Due to their negative electrical charge and absence of electrical charge, respectively, anionic-type compounds and non-ionic-type compounds are commonly less effective conditioning agents compared to cationic-type compounds. In view of their performance and solubility in water, cationic polymers are preferably used as conditioning agent and, at present, about 75 percent of the conventional cosmetic rinse-off compositions contain cationic polymers. Typical cationic polymers used as conditioning agent in rinse-off compositions are disclosed in WO 02/055036.

Commercially available cationic polymers include copolymers of vinyl-pyrrolidone and dimethylaminoethyl methacrylate quaternised with dimethyl sulfate (available as Gafquat®, trade name of International Specialty Products), homopolymers of dimethyldiallylammonium chloride and copolymers of dimethyldiallylammonium chloride and acrylamide (available as Merquat@, trade name of ONDEO Nalco), and (trimethyl-ammonium propyl ether) chloride derivatives of cellulose (available as UCARE™ Polymers, trade name of Amerchol).

A further class of ingredients, is constituted by so-called thickeners or viscosity improvers, namely ingredients that provide to the cosmetic rinse-off composition a desired viscosity, so that the composition appears, for example, in the form of a gel or cream, a viscous liquid, a pourable or a free flowing liquid. Furthermore, thickeners are also used to give physical stability to the rinse-off composition. In this respect, stability refers to the maintenance of the homogeneity of the composition. The thickener largely prevents the composition of separating into different liquid layers in case the composition is present in the form of an emulsion, prevents settling of a solid phase in case the composition is present in the form of a suspension, or prevents crystallisation of some of the ingredients. Typically used thickeners include xanthan gums, alginate salts, and cross-linked acrylic (co)-polymers, for example Tego Carbomer® (trade name of Degussa Care Specialties), and Carbopol® (trade name of Noveon). Cosmetic rinse-off compositions furthermore commonly comprise various additional ingredients, for example colouring agents, perfuming agents, anti-bacterial agents, pH-stabilising agents, anti-oxidants, and stabilisers to inhibit darkening resulting from chemical reactions of certain ingredients. So, desirable properties of a cosmetic rinse-off composition include on the one hand physico-chemical features, particularly an appropriate viscosity, physical stability, and good rinse-off properties, and on the other hand cosmetic effects on the hair, such as easy disentangling, soft feeling and good conditioning of the hair.

The composition is preferably an aqueous composition.

Shampoo

Compositions of the current invention may be formulated as shampoo for cleansing of hair. Shampoo compositions will comprise a pressure sensitive adhesive emulsion and a cleansing agent as described above.

The shampooing compositions of the current invention may also comprise other optional ingredients. Such ingredients include, but are not limited to; cationic surfactants, conditioning agents (as described above) and deposition polymers.

Cationic Surfactants:

The shampoo composition can optionally include one or more cationic co-surfactants included in an amount ranging from 0.01 to 10 w.t. %, more preferably from 0.05 to 5 w.t. %, most preferably from 0.05 to 2 w.t. %. Useful cationic surfactants are described above in relation to conditioning agents.

The cationic conditioning polymer will generally be present in compositions of the invention at levels of from 0.01 to 5 w.t. %, preferably from 0.05 to 1 w.t. %, more preferably from 0.08 to 0.5 w.t. %.

A shampoo composition of the present invention may preferably comprise a miscellar structured liquid having a viscosity in the range of from 1000 cPs to 15000 cPs, more preferably 4000 cPs to 9000 cPs, most preferably 5500 cPs to 6500 cPs as measured on a Brookfield DV2T Helipath viscometer, at 30° C. using a RV5 spindle at 10 RPM. Addition of salt, preferably an alkali metal salt, more preferably NaCl or KCl; or of a thickening polymer, for example Versathix, ex Croda may be used in the adjustment of the viscosity. The pH of a shampoo comprising the present composition is preferably 7 or greater. More preferably the pH of the composition is 7.5 or greater.

Conditioner

Compositions of the current invention may be formulated as conditioners for the treatment of hair. Conditioner compositions will comprise a pressure sensitive adhesive emulsion and a conditioning agent as described above.

The conditioning compositions of the current invention may also comprise other optional ingredients. Such ingredients include, but are not limited to; fatty material, deposition polymers and further conditioning agents.

Fatty Material:

Conditioner compositions of the invention preferably additionally comprise fatty materials. The combined use of fatty materials and cationic surfactants in conditioning compositions is believed to be especially advantageous, because this leads to the formation of a structured lamellar or liquid crystal phase, in which the cationic surfactant is dispersed.

By "fatty material" is meant a fatty alcohol, an alkoxylated fatty alcohol, a fatty acid or a mixture thereof.

Preferably, the alkyl chain of the fatty material is fully saturated.

Representative fatty materials comprise from 8 to 22 carbon atoms, more preferably 16 to 22. Examples of suitable fatty alcohols include cetyl alcohol, stearyl alcohol and mixtures thereof. The use of these materials is also advantageous in that they contribute to the overall conditioning properties of compositions of the invention.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof. The level of fatty material in conditioners of the invention is suitably from 0.01 to 15, preferably from 0.1 to 10, and more preferably from 0.1 to 5 percent by weight of the total composition. The weight ratio of cationic surfactant to fatty alcohol is suitably from 10:1 to 1:10, preferably from 4:1 to 1:8, optimally from 1:1 to 1:7, for example 1:3.

A conditioning composition of the present invention may preferably comprise a miscellar structured liquid having a viscosity in the range of from 1000 cPs to 450000 cPs, more preferably 50 000 to 250 000 cPs most preferably 145 000 cPs to 155 000 cPs at measured on a Brookfield DV2T Helipath viscometer, at room temperature, using a TA/TB bar spindle with a helical path at 0.5 RPM. The skilled formulator will know that the miscellar/lamellar structure is obtainable via standard processing routes. Optionally, addition of salt, preferably an alkali metal salt, more preferably NaCl or KCl may be used in the adjustment of viscosity.

The pH of a conditioner comprising the present composition is preferably 3-5. More preferably the pH of the composition is 4.5-5.5.

Other Components

Compositions of this invention may contain any other ingredient normally used in hair treatment formulations, including further silicone or non-silicone hair conditioning oils. These other ingredients may include viscosity modifiers, preservatives, colouring agents, polyols such as glycerine and polypropylene glycol, chelating agents such as EDTA, antioxidants, fragrances, antimicrobials and sunscreens. Each of these ingredients will be present in an amount effective to accomplish its purpose. Generally these optional ingredients are included individually at a level of up to 5% by weight of the total composition.

Use of the Composition

The claimed composition may be used in the treatment of hair to provide styling and/or restyling benefits. The styling and restyling benefits to be achieved particularly include reduction of frizz and volume, and providing an appropriate level of 'grip'. 'Grip' is temporary viscous drag, which provides the consumer with greater control when styling and blow drying the hair. 'Grip' can be measured by dynamic friction of the hair.

Method of Use

The rinse off hair treatment composition of the current invention as claimed and described above, may be used by a method comprising the following steps;

Apply to hair

Leave on hair for 0 to 10 minutes

Rinse off with water

EXAMPLES

Example 1: Comparison of Hair Styling Polymers

Hair switches were first washed. The switch was held under running water for 30 seconds, shampoo applied using a non-hypodermic syringe in a dose of 0.1 ml of shampoo per 1 g of hair and rubbed into the hair for 30 seconds. Excess lather was removed by holding under running water for 30 seconds and the shampoo stage repeated. Conditioner was then applied to the switch by a non-hypodermic syringe in a dose of 0.2 ml of conditioner per 1 g of hair and massaged into the switch for 1 minute. The switch was rinsed under running water for 1 minute, combed through 10 times using the fine end of a Matador 4 comb and excess water removed using a kim wipe.

The styling material was applied to the freshly washed hair switches in a dose of 0.05 g of styling material per 1 g of hair. The styling material was massaged thoroughly into the switch and combed through 5 times using the fine end of a Matador 4 comb. The switch was left to dry in an oven at 50° C. for 30 minutes.

The switches were then clamped and a straightening iron passed along the length of the switch 3 times. An image was taken—'Initial style'.

The switches were then placed on a switch oscillator in a humidity chamber set at 30° C. and 80% RH for 45 minutes to break the style. An image was taken—'Humidity and Agitation'.

The switches were re-styled by combing out all the knots and then combing through 10 times using the fine end of a matador 4 comb and one "finger slide" along the length of the switch. An image was taken—'Re-style'.

Images were analysed to access volume of the hair and data presented in table 1.

TABLE 1

| Material | Initial style | Humidity and Agitation | Re-style |
|---|---|---|---|
| Acudyne MD5800 (3%) | 5520 | 11520 | 7880 |
| MQ resin (3%) | 6400 | 11200 | 10360 |
| Luviquat Supreme (3%) | 5720 | 12200 | 13040 |
| Control (water) | 7360 | 13960 | 13240 |

Acudyne MD5800, is an acrylic PSA available from Dow Corning Acronal V215 is an Acrylic PSA material developed by BASF.MQ Resin is a silicone based PSA material developed by Dow Corning and are made of M organosiloxane (R3SiO1/2) monomers and Q siloxane monomers (SiO4/2). Luviquat Supreme (INCI Polyquaternium-68) is a cationic compound developed by BASF.

Example 2: Shampoo Composition

The shampoo compositions shown in Table 2 may prepared using the following method; Heating the water to 30° C. and stirring using an overhead stirrer and paddle (e.g. Heidolph). Adding the PSA emulsion and stirring until thoroughly mixed. Adding each of the remaining ingredients individually and allowing the composition to thoroughly mix between each addition. Adjusting the pH and viscosity as necessary using NaCl and NaOH.

Percentages are by weight.

TABLE 2

| Material | Weight % in composition |
|---|---|
| Acudyne MD 5800[1] (55% active) | 3.64% |
| Carbopol ® 980[2] (4% active) | 10% |
| Sodium hydroxide (50% active) | 0.43% |
| Sodium Laureth Sulphate (70% active) | 17.14% |
| Cocoamidopropyl betaine[3] (30% active) | 5.33% |
| Jaguar C14 S[4] | 0.2% |
| Others and water | To 100% |

[1]Acudyne MD5800 is an acrylic PSA available from Dow Corning
[2]Carbopol ® 980 is a crosslinked polyacrylate polymer available from Lubrizol
[3]supplied by Galaxy
[4]Jaguar C14 S is Guar Hydroxypropyl Trimonium Chloride polymer available from Rhodia Example 3: Conditioner Composition The hair conditioning composition shown in Table 3 may be prepared by the following method; Heating the water to 81° C. and stirring using an overhead stirrer and paddle (e.g. Heidolph). Mixing in the fatty materials and the surfactant. Maintaining heat and stirring for 30 minutes. Cooling the mixture and mixing in the remaining ingredients. Mixing at high shear for 5 minutes (e.g. using a Silverson mixer).

Percentages are by weight.

TABLE 3

| Material | Weight % in composition |
|---|---|
| Acudyne MD 5800[1] (55% active) | 0.91% |
| Lactic acid (85% active) | 0.38% |
| Stearamidopropyl Dimethylamine | 1.25% |
| Cetearyl Alcohol | 5.00% |
| Behentrimonium Chloride & Dipropylene Glycol[2] (68.5% active) | 1.25% |
| Sodium chloride | 0.10% |
| Silicone DC 5-7134[3] (70% active) | 0.50% |
| Others and water | To 100% |

[1]Acudyne MD5800 is an acrylic PSA available from Dow Corning
[2]trade name Genamin BTLF supplied by Aako
[3]Silicone DC 5-71334 supplied by Dow Corning Example 4: Preparation of Composition 1 in Accordance with the Invention and Comparative Compositions A and B Compositions 1, A and B were shampoo compositions.

Composition 1, in accordance with the invention, comprised 1% of pressure sensitive adhesive (PSA).

Comparative examples A and B did not comprise PSA. Comparative example B comprised 1% of MQ resin.

The compositions were made using the preparation methods described above and are shown in table 4 below.

TABLE 4

| | Compositions (wt %) of composition 1 and comparative compositions A and B | | |
|---|---|---|---|
| | Weight % in composition | | |
| Material | A 0% PSA | 1 1% PSA | B 1% MQ resin |
| Acrylates Copolymer (Acudyne MD 5800) (PSA) | 0 | 1.8182 | 0 |
| Carbomer | 0.4 | 0.4 | 0.4 |
| Sodium Hydroxide | 0.2 | 0.2 | 0.2 |
| Sodium Laureth Sulphate | 17.1429 | 17.1429 | 17.1429 |
| Cocamidopropyl Betaine | 5.3333 | 5.3333 | 5.3333 |
| Guar Hydroxypropyltrimonium Chloride | 0.2 | 0.2 | 0.2 |
| D5 and Trimethylsiloxysilicate and Dimethiconol (MQ resin) | 0 | 0 | 1 |
| Sodium Chloride | 1.2 | 1.2 | 1.2 |
| Minors and water | 75.5238 | 73.7056 | 74.5238 |

Example 5: Friction of Hair Treated with Composition 1 in Accordance with the Invention and Comparative Compositions A and B Hair used in the following examples was prepared as follows:

6" 2.5 g dark brown European (DBE) switches with wide flat metal clips were washed in sets of five (to provide five replicates per treatment). Each set of switches was washed using following protocol:

Switches were wetted under running flow controlled tap (water temperature 35-40° C., flow rate 4 L/min) and then excess water removed by running switches between thumb and forefinger.

The switches were then submerged in 14% SLES solution and immediately removed and any excess solution removed as above.

The switches were then agitated for 30 seconds, creating a lather whilst keeping hold of both end of the switches to prevent overly tangling the hair.

The switches were rinsed under the flow controlled tap for 30 seconds.

1.25 g shampoo (0.1 g per gram of hair) was applied to the length of the switches using a syringe and the switches then agitated for 30 seconds.

The switches were rinsed under the flow controlled tap for 30 seconds.

The shampoo and rinse step was repeated.

Any excess water was then removed from the switches and they were hung to dry in an ambient drying cabinet for 24 hours.

For leave on treatments, the hair was washed with 14% SLES as above and then 0.15 g product (0.05 g per gram of hair) applied to each individual switch. The treatment was spread across the switch for 60 seconds and the switch was then dried.

Tribology Method Used to Measure Friction of Hair:

Friction is known to aid styling and styling retention of hair. Tribology was used to show increase in friction in hair treated with Compositions 1, A and B.

Friction measurements were made using an Eldredge tribometer, a bespoke piece of equipment designed to measure friction, based on speed and load, between a stationary sample and a countersurface (in this instance a rubber TA probe) attached to a moving arm.

A sample (hair switch prepared as per TA switch washing method) was mounted into the clamp on the baseplate of the Eldredge. A clean rubber TA probe was mounted at the end of the arm, which was driven by a variable speed motor. A brass weight was placed on the arm (the weight will vary dependent on the type of test being conducted) and the arm was counterbalanced until it rested horizontally when the probe and sample surface were in contact. The stroke length was adjusted to fit the size of the hair switch (in this instance stroke length=60 mm). The speed of movement of the arm was set, dependent on test.

A weight ramp was produced by setting the arm to begin moving at a set speed (in this instance, speed setting 50=15.1617 mms$^{-1}$) with an initial weight of 10 g placed onto the arm. The arm completed a minimum of two full cycles of movement across the switch, and then the weight on the arm was changed for the next required weight.

| Order of weights used for weight ramp | 10 g | 20 g | 50 g | 100 g | 200 g |

Strain gauges, mounted on steel plates which attach the probe holder to the main arm, measure the degree of bending of the plates due to the frictional force exerted between the sample and countersurface. The strain gauges were attached in a full Wheatstone bridge configuration to a Fylde transducer amplifier. Measurements were recorded at 0.025 second intervals and output as voltage.

A minimum of three replicate switches were tested for each of composition 1, A and B. One rubber TA probe was used per composition, rotated slightly between replicates to provide a clean surface for each run.

Results thus obtained are given in Table 5 below.

TABLE 5

Friction of hair treated with Compositions 1, A and B (using 10 replicate switches)

| Weight/g | Rep1 | Rep2 | Rep3 | Rep4 | Rep5 | Rep6 | Rep7 | Rep8 | Rep9 | Rep 10 | Mean μ (rep1-10) |
|---|---|---|---|---|---|---|---|---|---|---|---|
| Comparative Composition A: 0% PSA | | | | | | | | | | | |
| 10 | 1.6561 | 1.8400 | 1.6414 | 1.7541 | 1.8606 | 1.7963 | 1.8041 | 1.9691 | 1.9245 | 2.0835 | 1.8330 |
| 20 | 1.5817 | 1.8503 | 1.5658 | 1.8191 | 1.8129 | 1.6091 | 1.8188 | 1.9537 | 1.8543 | 1.9699 | 1.7835 |
| 50 | 1.4856 | 1.6765 | 1.5125 | 1.7159 | 1.6960 | 1.5052 | 1.7001 | 1.7904 | 1.7442 | 1.8029 | 1.6629 |
| 100 | 1.4416 | 1.5918 | 1.4662 | 1.6431 | 1.6181 | 1.3750 | 1.6238 | 1.5394 | 1.6658 | 1.6738 | 1.5638 |
| 200 | 1.3658 | 1.4829 | 1.4020 | 1.5384 | 1.4923 | 1.3190 | 1.5261 | 1.5396 | 1.5821 | 1.5648 | 1.4813 |
| Comparative Composition B: 1% MQ resin | | | | | | | | | | | |
| 10 | 1.9184 | 1.8525 | 2.0614 | 1.8388 | 1.8020 | 1.9559 | 2.0797 | 1.9766 | 1.9326 | 1.7597 | 1.9178 |
| 20 | 1.6805 | 1.7466 | 1.8766 | 1.6582 | 1.5852 | 1.8277 | 1.9519 | 1.7940 | 1.8348 | 1.7461 | 1.7702 |
| 50 | 1.4801 | 1.5793 | 1.6682 | 1.4811 | 1.3841 | 1.6347 | 1.7178 | 1.5984 | 1.6604 | 1.6262 | 1.5830 |
| 100 | 1.3795 | 1.4716 | 1.5502 | 1.3750 | 1.2863 | 1.5060 | 1.6077 | 1.5064 | 1.5304 | 1.3948 | 1.4608 |
| 200 | 1.2672 | 1.2877 | 1.4221 | 1.3004 | 1.1878 | 1.3916 | 1.4614 | 1.3818 | 1.3926 | 1.2224 | 1.3315 |
| Composition 1: 1% PSA | | | | | | | | | | | |
| 10 | 2.2828 | 2.1276 | 2.7575 | 1.9643 | 2.3261 | 1.7857 | 1.9189 | 2.2473 | 2.2594 | 2.0532 | 2.1723 |
| 20 | 2.0841 | 2.0705 | 2.4277 | 1.8216 | 2.0917 | 1.7186 | 1.8734 | 2.1144 | 2.1463 | 1.7658 | 2.0114 |
| 50 | 1.9177 | 1.9028 | 2.1593 | 1.9512 | 1.9466 | 1.6371 | 1.8584 | 1.9749 | 2.0275 | 1.8528 | 1.9228 |
| 100 | 1.8385 | 1.8747 | 1.9877 | 1.8971 | 1.8723 | 1.6280 | 1.8578 | 1.9633 | 2.0370 | 1.8613 | 1.8818 |
| 200 | 1.6919 | 1.8648 | 1.8265 | 1.7844 | 1.7859 | 1.6178 | 1.8001 | 1.8855 | 1.9162 | 1.7677 | 1.7941 |

It will be seen that the 1% PSA formulation delivered statistically higher friction than the MQ resin and the control, at all weights.

Example 6: Friction of Hair Treated with a Rinse Off Composition in Accordance with the Invention and a Commercially Available Leave-on Product A commercially available leave-on product (Tigi Bedhead On the Rebound Curl Recall cream, which contained 9% w/w PSA) was tested for frictionalisation of hair, using the procedure described above.

A rinse off shampoo, comprising 1% PSA was also tested alongside the leave-on.

Results are given in Table 6.

TABLE 6

Comparison of friction resulting from the use of a rinse off shampoo composition, in accordance with the invention and a leave-on composition.

| Weight/g | Leave-on | Rinse off |
|---|---|---|
| 10 | 0.7462 | 1.5046 |
| 20 | 0.7600 | 1.6605 |
| 50 | 0.7383 | 1.7186 |
| 100 | 0.7098 | 1.7162 |
| 200 | 0.6360 | 1.6874 |

Surprisingly, it will be seen that the rinse off composition provided higher friction to hair, despite the lower level of PSA.

Example 7: Panel Test for the Assessment of Tack

Hair that has "tack" exhibits better stylability and restylability properties. Tack creates adhesion between fibres in desired hair-style conformation under pressure, thus aiding in style creation or restyling.

Preparation of Hair Switches

Hair switches were prepared following the protocol given above, with the following changes: 10" 7 g dark brown European (DBE) switches with flat metal clips were prepared individually. 0.7 g shampoo (0.1 g per gram of hair) was applied to the length of the switch using a syringe and the switch was then agitated for 30 seconds. Three switches were prepared per treatment, to allow for the three replicates of the test.

Sensory Assessment

The switch assessments were blind tests, with switches presented to each trained panellist in a random order and labelled with an arbitrary three digit number. The panellists are led through the test using FIZZ software and were asked to rank the switches from most to least for the attribute, tack.

The output from the FIZZ software was then used to provide mean ranks for the products and determine the statistical significance between these results.

The results are shown in table 7 below, where a lower number indicates greater tack.

TABLE 7

Tack of hair treated with Compositions 1, A and B.

| | Tack | | |
|---|---|---|---|
| | 0% PSA | 1% PSA | 1% MQ resin |
| Scores | 36 | 36 | 36 |
| Min | 1 | 1 | 1 |
| Max | 3 | 3 | 3 |
| Range | 2 | 2 | 2 |
| Mean | 2.69 | 1.17 | 2.14 |
| Std. Dev. (n) | 0.52 | 0.44 | 0.58 |
| Std. Dev. (n − 1) | 0.52 | 0.45 | 0.59 |
| Var. Coeff. (%) | 19.48 | 38.33 | 27.72 |
| Conf. Int. 5% ± | 0.18 | 0.15 | 0.2 |
| Conf. Int. 1% ± | 0.24 | 0.2 | 0.27 |

Inter-product significant differences at 95% confidence interval are shown in Table 8 below.

TABLE 8

| Sensory attributes | Tack |
|---|---|
| 0% PSA | A |
| 1% PSA | B |
| 1% MQ resin | A |

Same letter denotes no significant difference

Different letters denote significant difference at 95% confidence interval

It can be seen that the formulation in accordance with the invention gives greater tack, which is directly linked to better stylability and restylability.

Example 8: Expert Assessment of Volume, Ease of Style Creation and Grip in Hair Treated with Compositions 1, A and B These tests were carried out by an expert salon stylist. The stylist applied products (Compositions 1, A and B) to mannequin heads and assessed the products and hair for volume, ease of style creation and grip. The heads had dark brown European straight, layered normal texture hair, and are base washed in a non-conditioning shampoo formulation prior to beginning the test. For the half-head protocol, hair was split equally down the centre of the head into two sections, one either side of the head. Equal volumes of two products were applied to either side of the head. The head was washed with the test products and dried and styled using a hairdryer, with assessment of the chosen attributes occurring at each stage.

The attributes volume, ease of style creation and grip were assessed. The results are given in Table 9 below.

TABLE 9

| Attribute | Attribute type | Composition B: 1% MQ Resin | Composition 1: 1% PSA | Composition A: Control 0% active |
|---|---|---|---|---|
| Ease of style creation | Styling | 5 | 7 | 5.5 |
| Grip | Styling | 5 | 7 | 4 |
| Volume | Post styling | 5 | 7 | 5.5 |

It will be seen that the composition in accordance with the invention delivered greater volume, ease of style creation and grip to hair.

The invention claimed is:

1. A rinse off hair treatment composition consisting of:
   a. a pressure sensitive adhesive emulsion comprising an active pressure sensitive polymer, wherein the active pressure sensitive polymer is not a silicone pressure sensitive polymer, and wherein the active pressure sensitive polymer is an acrylic pressure sensitive copolymer having:
      i) an acrylic group having a side-chain with at least 4 carbons; and
      ii) an acrylic group having a C1-C6 side chain,
   b. at least one material selected from the group consisting of
      i) a hair conditioning agent; and
      ii) a hair cleansing agent, and c. a deposition polymer selected from the group consisting of cationic cellulose and cationic guar gum derivatives,
d. water, and
e. optionally, other ingredients;
wherein the active pressure sensitive polymer is present at 0.01 to 10 wt. % in the rinse off hair treatment composition.

2. The rinse off hair treatment composition according to claim 1, wherein the particle size of the pressure sensitive adhesive emulsion is 1 nm to 1 um.

3. The rinse off hair treatment composition according to claim 1, wherein the acrylic group having a side chain with at least 4 carbons is butyl acrylate and the acrylic group having a C1-C6 side chain is methacrylic acid.

4. The rinse off hair treatment composition according to claim 1, wherein the rinse off composition is a shampoo or conditioner composition.

5. The rinse off hair treatment composition according to claim 4, which is a shampoo, wherein the pH is 7 or greater.

6. The rinse off hair treatment composition according to claim 1, wherein the composition is a shampoo composition comprising a micellar structured liquid having a viscosity in the range of from 1,000 cPs to 15,000 cPs as measured on a Brookfield DV2T Helipath viscometer, at 30° C. using a RV5 spindle at 20 RPM.

7. A rinse off hair treatment composition according to claim 1, wherein the composition is a conditioning composition comprising a micellar structured liquid having a viscosity in the range of from 1,000 cPs to 450,000 cPs at measured on a Brookfield DV2T Helipath viscometer, at room temperature, using a TA/TB bar spindle with a helical path at 0.5 RPM.

8. A method of treating hair comprising:
applying to the hair a rinse off hair treatment composition as defined in claim 1,
leaving the composition on the hair for less than one minute to 10 minutes, and
rinsing the composition off of the hair.

9. The rinse off hair treatment composition according to claim 1 wherein the acrylic group having a side chain with at least 4 carbons is selected from the group consisting of n-butyl acrylate, butyl acrylate, 2-ethylhexyl acrylate, n-hexyl acrylate, isooctyl acrylate and dodecyl acrylate, and the acrylic group having a C1-C6 side chain is selected from the group consisting of acrylic acid, methyl acrylate, methyl methacrylate, methacrylic acid, ethyl acrylate, and butyl acrylate.

10. The rinse off hair treatment composition of claim 1, wherein the other ingredients are selected from the group consisting of cationic surfactants, suspending agents, thickeners, viscosity modifiers, silicone hair conditioning oils, non-silicone hair conditioning oils, preservatives, stabilizers to inhibit darkening, coloring agents, polyols, chelating agents, antioxidants, fragrances, perfuming agents, antimicrobials, sunscreens, lactic acid, stearamidopropyl dimethylamine, cetearyl alcohol, an alkali metal salt, sodium hydroxide, carbomer, sodium laureth sulphate, and cocamidopropyl betaine.

* * * * *

UNITED STATES PATENT AND TRADEMARK OFFICE
CERTIFICATE OF CORRECTION

| | | |
|---|---|---|
| PATENT NO. | : 11,103,438 B2 | Page 1 of 1 |
| APPLICATION NO. | : 15/543684 | |
| DATED | : August 31, 2021 | |
| INVENTOR(S) | : Christopher David Bentley et al. | |

It is certified that error appears in the above-identified patent and that said Letters Patent is hereby corrected as shown below:

On the Title Page

Item (73) Assignee: "Conopeo, Inc." should be corrected to read --Conopco, Inc.--

Signed and Sealed this
Fifteenth Day of April, 2025

Coke Morgan Stewart
*Acting Director of the United States Patent and Trademark Office*